US006602292B2

(12) United States Patent
Burkinshaw (10) Patent No.: US 6,602,292 B2
(45) Date of Patent: Aug. 5, 2003

(54) MOBILE BEARING PATELLA PROSTHESIS

(75) Inventor: Brian D. Burkinshaw, Pflugerville, TX (US)

(73) Assignee: Centerpulse Orthopedic Inc., Austin, TX (US)

( * ) Notice: Subject to any disclaimer, the term of this patent is extended or adjusted under 35 U.S.C. 154(b) by 0 days.

(21) Appl. No.: 09/923,238

(22) Filed: Aug. 3, 2001

(65) Prior Publication Data

US 2002/0128719 A1 Sep. 12, 2002

Related U.S. Application Data

(60) Provisional application No. 60/273,789, filed on Mar. 6, 2001.

(51) Int. Cl.[7] .................................................. A61F 2/38
(52) U.S. Cl. ..................................................... 623/20.2
(58) Field of Search ........................... 623/20.16, 20.18, 623/20.19, 20.2, 18.11, 16.11

(56) References Cited

U.S. PATENT DOCUMENTS 4,041,550 A * 8/1977 Frazier .................... 623/20.19
5,263,992 A * 11/1993 Guire ......................... 436/501
5,609,644 A * 3/1997 Ashby et al. .............. 623/20.2
5,702,465 A * 12/1997 Burkinshaw ............... 623/20.2
5,723,016 A * 3/1998 Minns et al. ............... 623/20.2

* cited by examiner

Primary Examiner—Corrine McDermott
Assistant Examiner—William H. Matthews
(74) Attorney, Agent, or Firm—Kenneth S. Barrow (57) ABSTRACT

An implantable patellar prosthesis accommodates variations in placement of the prosthesis relative to the patella without limiting use of the prosthesis. The prosthesis utilizes a base component having a fixation portion for fixation to patellar bone. Additionally, the device uses an articulation component that may move relative to the base component. A coupling mechanism is provided for coupling the articulation component to the base component while permitting relative motion of the articulation component with respect to the base component. This relative motion can be controlled according to the design of the prosthesis and facilitates implantation as well as use of the prosthesis.

13 Claims, 9 Drawing Sheets

MOBILE BEARING PATELLA PROSTHESIS

This application claims priority to provisional application No. 60/273,789 filed on Mar. 6, 2001 and incorporated herein by reference.

FIELD OF THE INVENTION

The present invention relates generally to implantable orthopedic prostheses, and more particularly to implantable patellar prostheses for use at the knee joint.

BACKGROUND OF THE INVENTION

Generally, the human knee joint comprises three bones, the femur, the tibia and the patella, which each have a smooth surface for articulation on an adjacent surface of at least one other bone. At its distal extremity, the femur has an articulation surface with medial and lateral convex condyles separated posteriorly by an intercondylar groove running generally in the anterior-posterior direction. The condyles join at the distal-anterior face of the femur to form a patellar surface having a shallow vertical groove as an extension of the intercondylar groove.

The patella includes on its posterior face an articulation surface having a vertical ridge separating medial and lateral convex facets. These facets articulate against the patellar surface of the femur and against the medial and lateral condyles during flexing of the knee joint. The vertical ridge rides within the intercondyler groove to prevent lateral displacement of the patella during flexing of the knee joint.

At its proximal end, the tibia includes an articulation surface having medial and lateral meniscal condyles that articulate against the medial and lateral condyles, respectively, of the femur. The mutually engaging articulation surfaces of the femur and the patella together form the patellofemoral joint and the mutually engaging articulation surfaces of the femur and tibia form the tibiofemoral joint. These two functional joints form the anatomical knee joint.

Because of disease or trauma, all or part of one or more of the articulation surfaces of the knee joint may fail to perform properly. This can lead to a need or desirability for replacement of the defective natural articulation surface with a prosthetic articulation surface of an implantable prosthesis. A range of orthopedic implants is available, including patella prostheses used to replace the natural articulation surface of the patella. Such replacements may be accomplished by surgically resecting the patella to remove the posterior portion of the bone, leaving a planar bony surface to which a patellar prosthesis is affixed. The patellar prosthesis typically has an affixation surface affixed to the resected bony surface of the patella with, for example, bone cement. The prosthesis also typically includes an articulation surface that may be made of a biocompatible synthetic polymer material, such as ultrahigh molecular weight polyethylene.

Proper anatomic function of the knee joint is facilitated by proper placement of the prosthetic articulation surface or surfaces during surgery. If the affixation surface is properly affixed to the bony surface of the patella, the prosthetic articulation surface of the patella tracks the intercondylar groove and anterior patellar surface of the femoral prosthesis. During surgery, it is also important and sometimes difficult to mount the patellar prosthesis with proper angular placement.

It would be desirable to have patellar prosthesis designs that reduced or eliminated problems otherwise associated with medial-lateral or angular misplacement of the patellar prosthesis. It also would be desirable to have patellar prosthesis designs able to better simulate natural movement of the patella that occurs during flexing of the knee joint.

SUMMARY OF THE INVENTION

The present invention is generally directed to an implantable patella prosthesis. The prosthesis comprises a base component having a fixation portion that allows the base component to be affixed to patellar bone. The prosthesis also includes an articulation component that moves relative to the base component. Additionally, a coupling mechanism is designed to couple the articulation component and the base component in a manner that permits a more desirable movement of the articulation component relative to the base component during flexing of the human knee joint. This permits an individual to more readily adapt to the prosthetic device and also compensates for medial-lateral and/or angular misplacement of the patellar prosthesis during surgery.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENTS

Figure 1:
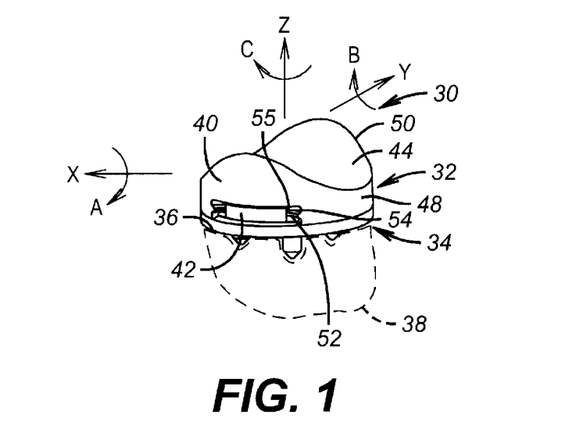
FIG. 1 is an isometric view of an implantable patellar prosthesis, according to an exemplary embodiment of the present invention.
Figure 2:
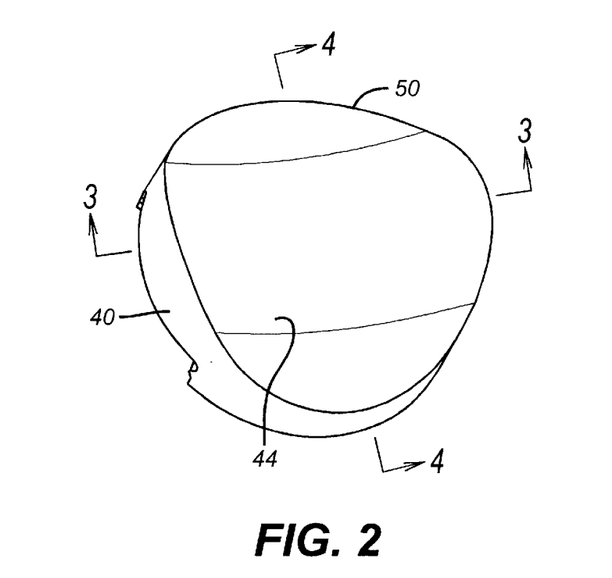
FIG. 2 is an isometric view taken from an upper or top position of the bearing member used with the prosthesis of FIG. 1.
Figure 3:
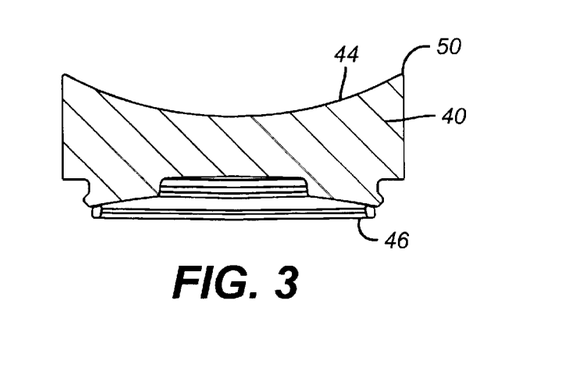
FIG. 3 is a cross-sectional view taken generally line 3—3 of FIG. 2.
Figure 4:
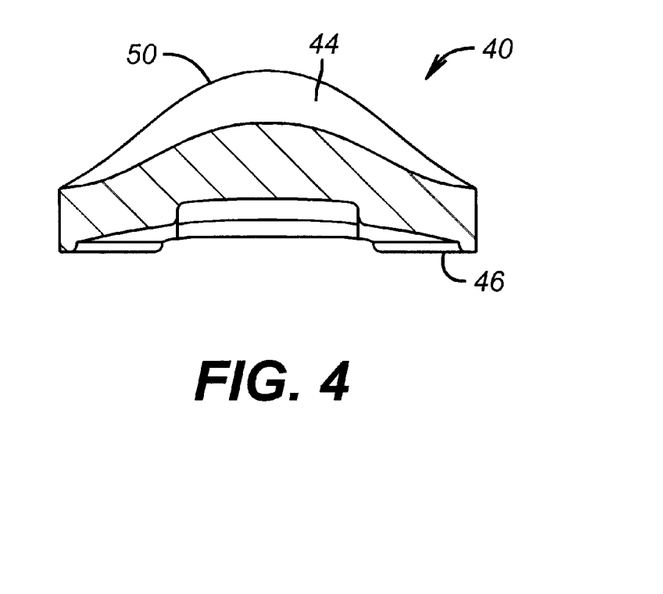
FIG. 4 is a cross-sectional view taken generally along line 4—4 of FIG. 2.

Referring generally to FIG. 1, an implantable patellar prosthesis 30 is illustrated according to one exemplary embodiment of the present invention. Prosthesis 30 comprises an articulation component 32 and a base component 34. Articulation component 32 is permitted to move relative to base component 34. This movement can be better understood by defining the six conventional axes used to describe component motion. As illustrated in FIG. 1, the three translational axes are labeled X, Y and Z and are mutually orthogonal to one another. The rotational axes A, B and C define rotational movement about each of the translational axes. Specifically, rotational axis A defines rotational movement about translational axis X; rotational axis B defines rotational motion about translational axis Y; and rotational axis C defines rotational motion about translational axis Z.

When prosthesis 30 is implanted, translational reference axes X, Y and Z correspond generally to well known and accepted anatomical directional terms. The X axis extends generally in the medial-lateral direction; the Y axis extends generally in the inferior-superior direction; and the Z axis extends generally in the posterior-anterior direction. For example, if we assume the prosthesis 30 is implanted on the left patella of a human patient, the ends of each of the X, Y and Z axes marked with an arrowhead point generally in the lateral, superior and posterior directions, respectively. During implantation, the patella bone is resected in a plane generally perpendicular to the anterior-posterior direction to remove a posterior portion of the patellar bone, leaving a resected planar bony surface 36. When the implantation is complete, the Z axis lies generally perpendicular to the resected bony surface 36 of a patella 38.

Articulation component 32 is constructed of an appropriate biocompatible material having desirable wear and bearing friction properties. Combinations of materials may be used when articulation component 32 is formed from multiple components. In the embodiment illustrated in FIG. 1, for example, articulation component 32 comprises a patella bearing portion 40 and a patella insert 42. In this embodiment, patella insert 42 is formed from a biocompatible material, such as titanium, titanium alloys, zirconia ceramics, aluminum oxide ceramics, cobalt chromium alloys and carbon-based materials, e.g. diamond or diamond compound. Patella bearing portion 40 also is made of suitable biocompatible materials, such as polyethylene, e.g. ultra-high molecular weight polyethylene, or ceramic materials.

The two-part configuration of articulation component 32 facilitates the use of dissimilar materials to form patella portion 40 and patella insert 42. This permits the use of a material for patella insert 42 that has little wear or degradation over extended periods of use. For example, the base component 34 and patella insert 42 can both be made from metal materials or ceramic materials to form, for example, metal on metal or ceramic on ceramic interfaces without interfering with material selection for patella portion 40.

Articulation component 32 is defined by an articulation surface 44, an interior surface 46 and a perimeter surface 48 extending generally between interior surface 46 and articulation surface 44. In this exemplary embodiment, articulation surface 44 is formed in a "saddle" shape in which the intersection of articulation surface 44 and perimeter surface 48 defines an undulating edge 50. An exemplary saddle shape is a hyperbolic paraboloid. This exemplary configuration of articulation surface 44 provides congruent sliding contact over an extensive range of articulation between articulation component 32 and a corresponding patellar articulation surface of a femoral component at the patellofemoral joint. The high points of the saddle (greatest distance between articulation surface 44 and interior surface 46) define a ridge that tracks the intercondylar groove of the femoral component during flexing of the knee joint.

Patella bearing portion 40 comprises a recessed portion, such as a pair of opposed, recessed regions 52, each having a retention feature 54 for holding patella insert 42. An exemplary retention feature 54 comprises a radially extending ridge or lip 55 designed to engage a corresponding feature of patella insert 42, such as a hook portion 56 extending radially inward to engage retention feature 54. Thus, patella bearing portion 40 and patella insert 42 may be securely snapped together for interaction with base component 34.

Figure 5:
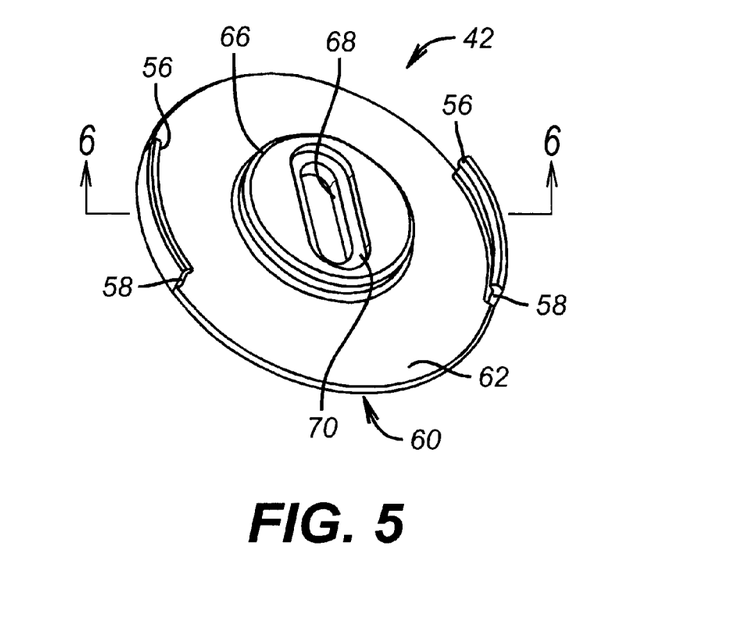
FIG. 5 is an upper isometric view of the patellar insert utilized in the design of FIG. 1.
Figure 6:
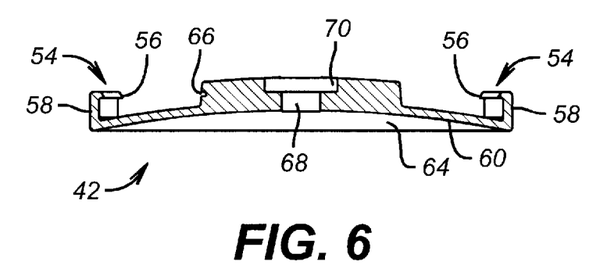
FIG. 6 is a cross-sectional view taken generally along line 6—6 of FIG. 5.

As illustrated best in FIGS. 5 and 6, hook portions 56 are mounted on tabs 58 that extend generally axially from a plate structure 60. Plate structure 60 comprises an interior surface 62 and a slide surface 64 designed for sliding contact with base component 34. In this embodiment, slide surface 64 is contoured for mating engagement with a corresponding contoured surface of base component 34, as described more fully below. One exemplary contour is that of a partial sphere.

Patella insert 42 also includes a generally centralized boss region 66 having a slot 68. Slot 68 extends through boss region 66 from interior surface 62 to sliding surface 64. A recessed region 70 also may be formed in boss region 66 along interior surface 62 and generally around slot 68, as illustrated best in FIGS. 5 and 6.

Base component 34 is constructed of a suitable, biocompatible material having desirable wear, bearing friction and bone engaging properties. Exemplary materials include titanium, titanium alloys, zirconia ceramics, aluminum oxide ceramics and cobalt chromium alloys. As illustrated best in FIGS. 7 and 8, base component 34 comprises a fixation portion 72 for engaging patellar bone 36. Fixation portion 72 comprises a fixation surface 74 and a plurality of protrusions 76, such as three pins. The pins extend generally in the anterior direction for insertion into corresponding receiving areas in patellar bone 36.

Figure 7:
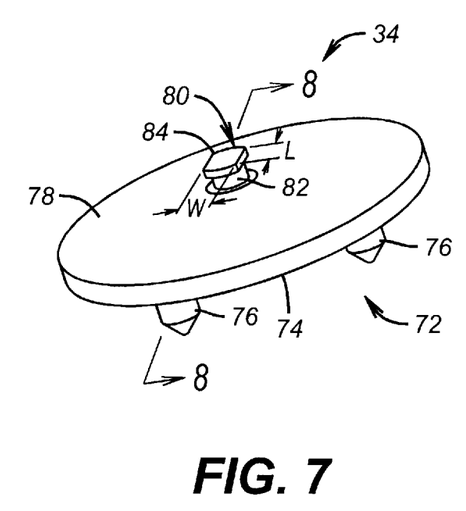
FIG. 7 is an upper perspective view of the patellar base utilized in the prosthesis illustrated in FIG. 1.
Figure 8:
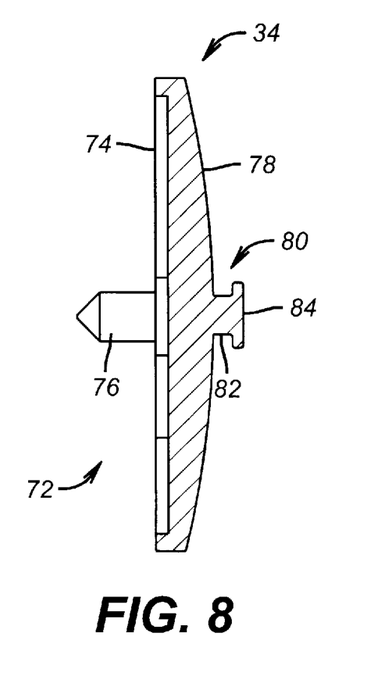
FIG. 8 is a cross-sectional view taken generally along line 8—8 of FIG. 7.

Opposite fixation portion 72, base component 34 has a bearing slide surface 78. In this embodiment, slide surface 78 is contoured for correspondence with slide surface 64 of articulation component 32. For example, slide surface 78 may be in the form of a partial sphere that corresponds to a partial sphere configuration of surface 64 to permit movement of articulation component 32 in an arc along slide surface 78 of base component 34.

Base component 34 further includes a retention pin 80 having a neck portion 82 and an expanded head portion 84. Head portion 84 has a lengthwise dimension L that is greater than its widthwise dimension W (see FIG. 7). Thus, the exemplary retention pin 80 has a T-pin configuration that allows the pin to be inserted through slot 68 and rotated for retention in recessed region 70 of boss 66. In other words, articulation component 32 may readily be attached and detached from base component 34 during the implantation procedure or during subsequent surgical procedures performed on the knee joint.

Assembly of the base component 34 and articulation component 32 simply requires movement of the slide surface 64 towards contoured surface 78 of base component 34. The articulation component is oriented such that width dimension (W) of head portion 84 moves through slot 68. Once through, articulation component 32 is rotated, e.g. approximately 90°, until the longer dimension (L) of head portion 84 is held in boss 66 by recessed region 70. The 90° rotation also places articulation surface 44 in proper alignment for sliding contact between articulation component 32 and the corresponding intercondylar groove of the femoral component during flexing of the knee joint. Later removal of articulation component 32 simply requires a reversal of these process steps including rotating the articulation component until the longer dimension (L) of head portion 84 is aligned with the length of slot 68. The articulation component is then moved away from the base component until retention pin 80 is fully withdrawn.

Retention pin 80 and slot 68 cooperate to provide a coupling mechanism for securely coupling articulation component 32 to base component 34 while allowing medial-lateral movement of articulation component 32 during reconstruction and use of the knee joint. This type of coupling mechanism also allows automatic angular adjustment of articulation component 32 relative to base component 34 by permitting rotational movement of articulation component about retention pin 80, i.e. about the Z axis. Furthermore, corresponding surfaces 64 and 78 of articulation component 32 and base component 34, respectively, can be used to control relative movement of the components. With spherical contours, for example, the movement of articulation component 32 is generally constrained to rotational motion about the Y axis, if we assume for the moment that the Y axis intersects the radial center of the arc selected to form slide surface 64. In this manner, the movement of articulation component 32 is restricted to two (2) degrees of freedom, i.e. rotational motion about the Z axis and rotational motion about the Y axis (assuming the Y axis to be at the radial center of the arc). This controlled motion tends to facilitate a less stressful interaction of the prosthesis with the natural form of a typical knee joint.

Fixation portion 72 is designed for connection to patellar bone 36 along the resected planar bony surface via a mantel of bone cement. Fixation surface 74 may be designed to facilitate osseointegration by providing surface texturing. Such surface texturing can be formed by a coating of hydroxyapatite, other ceramics or porous metal. These coatings may be applied by plasma spraying of powdered material or, for porous metal coatings, by sintering powdered metal or beads. Exemplary and suitable metals comprise titanium, titanium alloys and cobalt chromium alloys.

Protrusions 76, of course, also facilitate adherence of base component 34 to the patellar bone 36 when received in corresponding shaped bores (not shown) formed in the patellar bone. The protrusions 76 may be generally straight-sided or provided with a waist of reduced diameter. Additionally, protrusions 76 can be formed with a variety of macro-textured surface profiles to enhance fixation to patellar bone 36 by bone cement and/or osseointegration.

Figure 9:
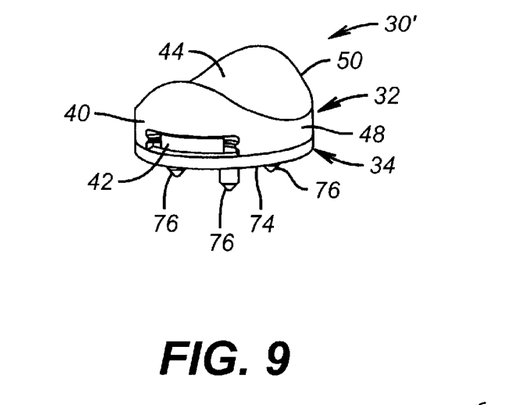
FIG. 9 is an isometric view of an alternate embodiment of the prosthesis illustrated in FIG. 1.
Figure 10:
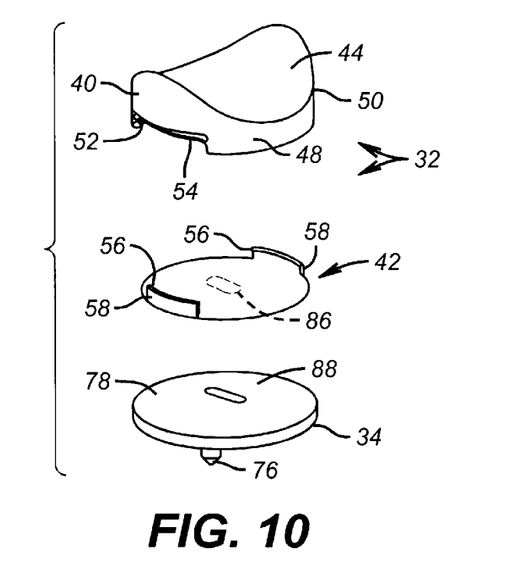
FIG. 10 is an exploded view of the prosthesis illustrated in FIG. 9.
Figure 11:
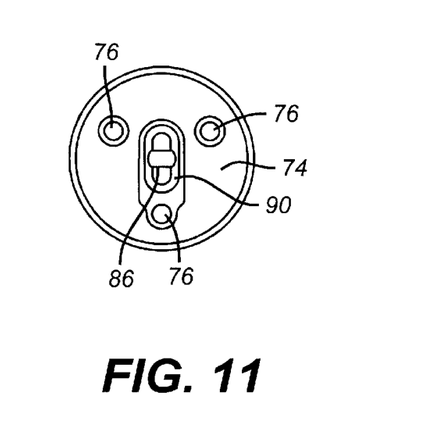
FIG. 11 is a bottom view of the prosthesis illustrated in FIG. 9.
Figure 12:
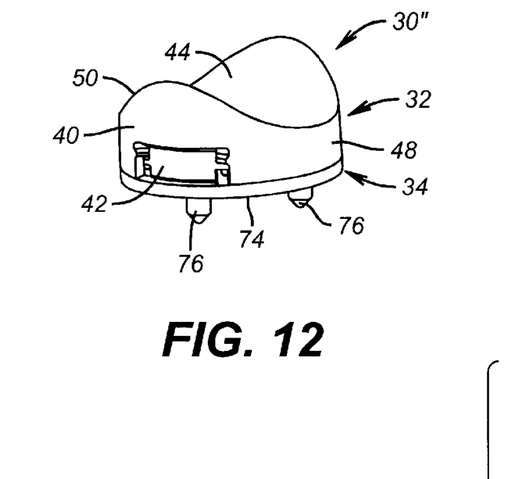
FIG. 12 is an isometric view of an alternate embodiment of the prosthesis illustrated in FIG. 1.
Figure 13:
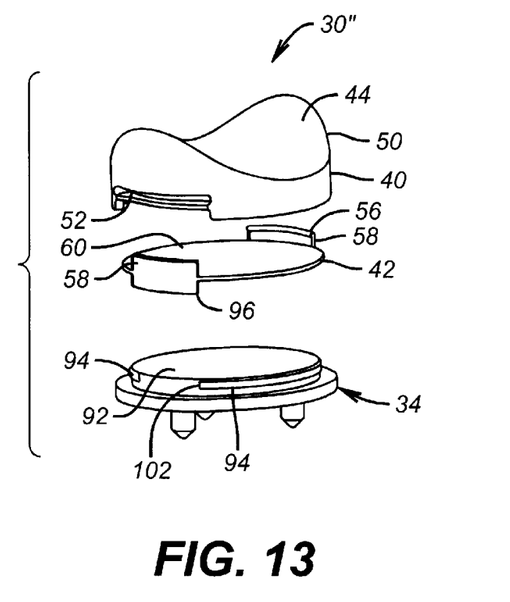
FIG. 13 is an exploded view of the prosthesis illustrated in FIG. 12.

Referring generally to FIGS. 9 through 11, an alternate embodiment of implantable patellar prosthesis 30 is illustrated and labeled as 30'. In this embodiment, the coupling mechanism for combining base component 34 with articulation component 32 is generally reversed. Also, it should be noted that common reference numerals are used with individual components that are the same or similar to corresponding components of the embodiment illustrated in FIGS. 1 through 8.

In this embodiment, however, a retention pin 86, such as a T-pin, extends from patella insert 42 for interaction with a slot 88 formed in base component 34. Slot 88 extends generally axially through base portion 34 from slide surface 78, e.g. a contoured slide surface, to fixation surface 74. Typically, a recessed region 90 is formed in fixation surface 74 around the perimeter of slot 88 to receive the T-shaped head portion of retention pin 86 upon rotation of articulation component 32 after insertion of retention pin 86 through slot 88. Thus, motion control is achieved similar to that described with reference to FIGS. 1 through 8 but with a coupling mechanism that utilizes a pin extending from the articulation component into cooperation with a corresponding slot formed in the base component.

Another alternate embodiment of implantable patellar prosthesis 30, labeled 30", is illustrated in FIGS. 12 through 16. As in the embodiments described above, articulation component 32 comprises patella bearing portion 40 and patella insert 42. Patella bearing portion 40 may be formed with a saddle shape or other suitable shapes and may be made from a variety of biocompatible materials, such as ultrahigh density polyethylene. Patella insert 42 is attached to patella bearing portion 40 by axially extending tabs 58 and hook portions 56 that snap over retention features 54 of patella bearing portion 40.

In this embodiment, however, implantable patellar prosthesis 30" utilizes an alternate coupling mechanism by which articulation component 32 is coupled to base component 34. Base component 34 comprises a hub portion 92 designed to serve as a pivot for articulation component 32. In other words, hub portion 92 permits rotational movement of articulation component 32 about the Z axis when base component 34 is fixed to patellar bone 36. Although a variety of pivot mechanisms might be utilized, the exemplary embodiment has a circumferential engagement region 94 that extends at least partially about the perimeter of hub portion 92. Patella insert 42 comprises a retention feature 96 designed to engage circumferential engagement region 94.

Figure 14:
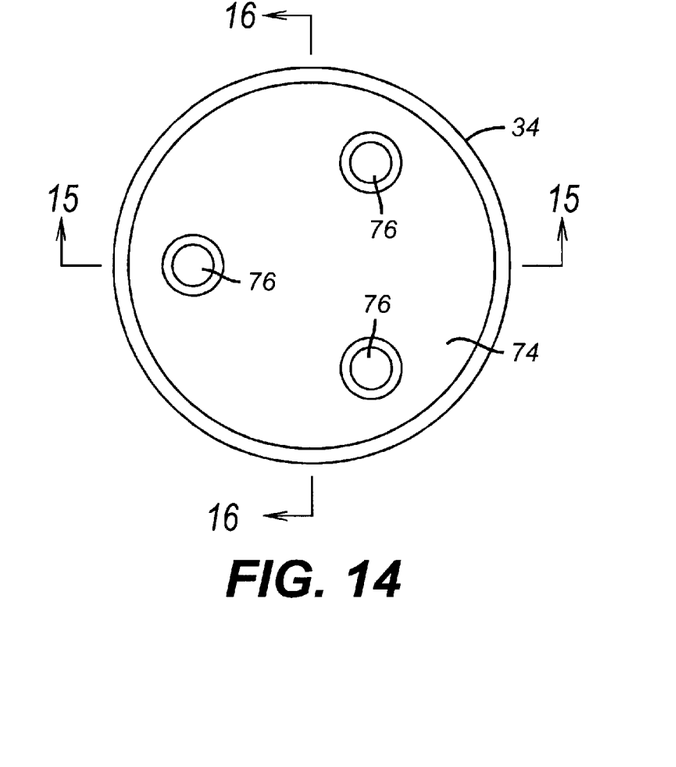
FIG. 14 is a bottom view of the prosthesis illustrated in FIG. 12.
Figure 15:
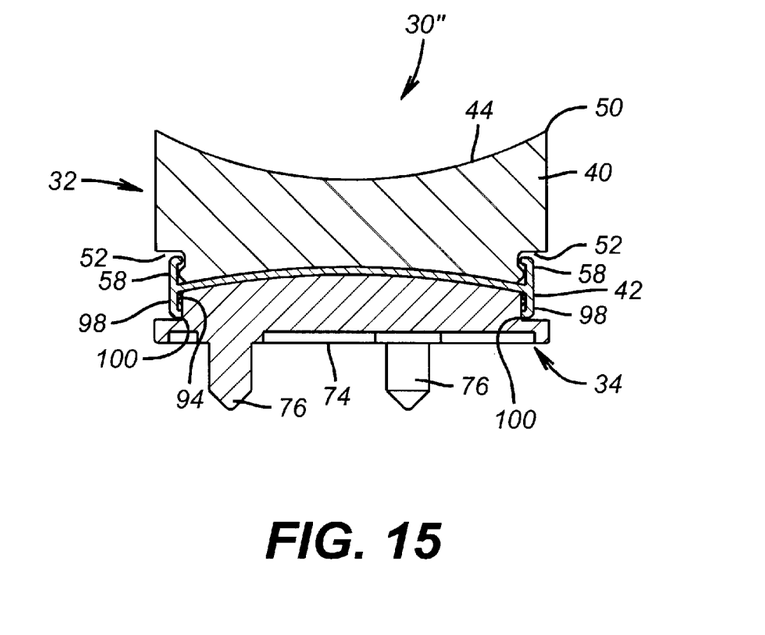
FIG. 15 is a cross-sectional view taken generally along line 15—15 of FIG. 14.

Specifically, retention feature 96 utilizes a pair of tabs 98 having hook portions 100 that grip circumferential engagement region 94, as best illustrated in FIGS. 14 and 15. Circumferential engagement region 94 is interrupted by a pair of gaps 102 that are at least as long as tabs 98. Thus, during engagement and disengagement of articulation component 32 with base 34, tabs 98 are aligned with gaps 102 and the components are moved together. Once hook portions 100 pass circumferential engagement region 94, articulation component 32 is rotated until hook portion 100 and articulation component 32 are held in place by engagement region 94. This rotation also places articulation surface 44 in proper alignment for sliding contact between articulation component 32 and the corresponding intercondylar groove of the femoral component during flexing of the knee joint. Removal of articulation component 32 requires rotation of articulation component 32 with respect to base component 34 until tabs 98 are aligned with gap 102. The articulation component then may be moved away from base component 34.

The interface between base component 34, patella insert 42 and patella bearing portion 40 may be generally flat.

Figure 16:
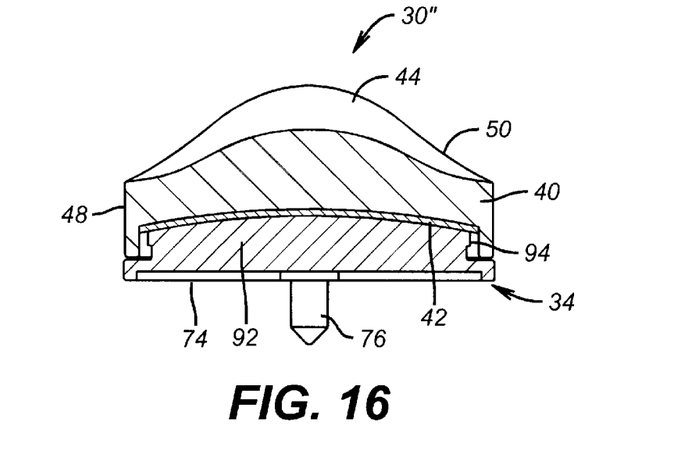
FIG. 16 is a cross-sectional view taken generally along line 16—16 of FIG. 14.

However, alternate interfaces may be formed along a variety of contours, such as the generally spherical contour illustrated best in FIGS. 15 and 16. The inverse of the illustrated contour as well as a variety of other contours also can be utilized. For example, the arcuate contour illustrated in FIGS. 15 and 16, may be beneficial for certain materials by increasing the strength and fracture resistance of patella bearing portion 40.

Figure 17:
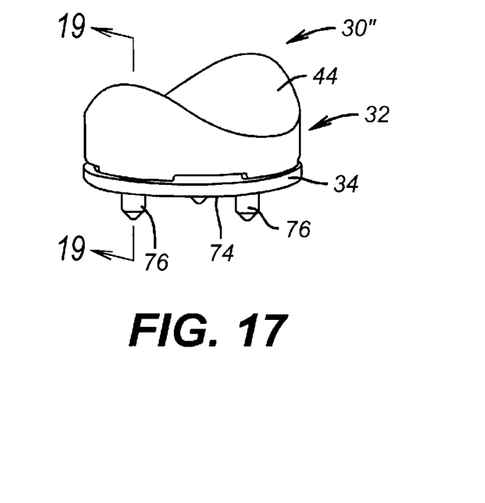
FIG. 17 is an isometric view of an alternate embodiment of the prosthetic device illustrated in FIG. 1.
Figure 18:
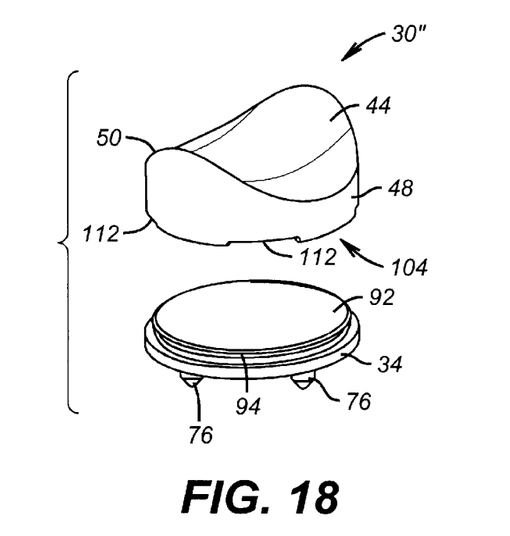
FIG. 18 is an exploded view of the prosthesis illustrated in FIG. 17.
Figure 19:
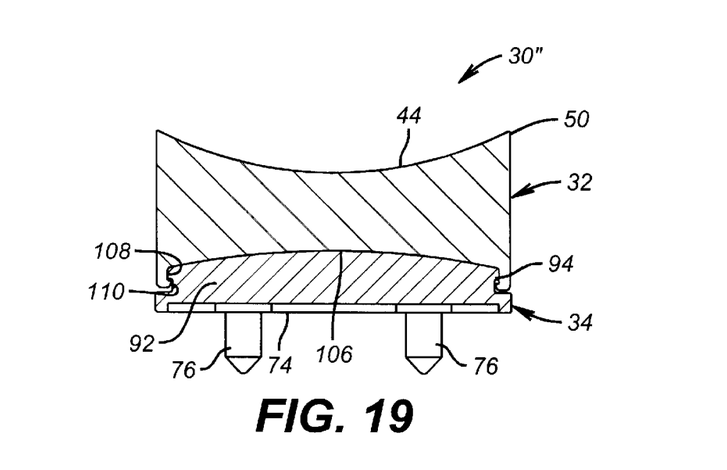
FIG. 19 is a cross-sectional view taken generally along line 19—19 of FIG. 17.

In a modified version of the implantable patellar prosthesis 30", a unitary articulation component 32 is used, as illustrated best in FIGS. 17 through 19. In this embodiment, a separate patella insert is not necessary. Rather, a unitary articulation component 32 is formed with a base engagement region 104 generally opposite articulation surface 44. Base engagement region 104 is designed to cooperate with hub portion 92 and circumferential engagement region 94. Specifically, base engagement region 104 includes a recessed area 106 having an annular groove 108 and a ridge 110 extending radially inwardly to capture and retain circumferential engagement region 94 within annular groove 108. To facilitate assembly and disassembly of articulation component 32 and base component 34, a series of gaps 112 can be formed in ridge 110 to facilitate flexure of ridge 110 over circumferential engagement region 94 during assembly and disassembly. Alternatively, a series of interruptions or gaps can be formed in circumferential engagement region 94, as described above and as illustrated in FIG. 13. The gaps permit insertion of corresponding portions of ridge 110 prior to rotation of articulation component 32 to capture circumferential engagement region 94 in annular groove 108, as illustrated best in FIG. 19.

As described with respect to the previous embodiment, the interface between articulation component 32 and base component 34 can vary depending on various design parameters. For example, the interface can be generally planar, convex-concave, concave-convex or a variety of other contours depending on types of materials used, required strength, etc.

Figure 20:
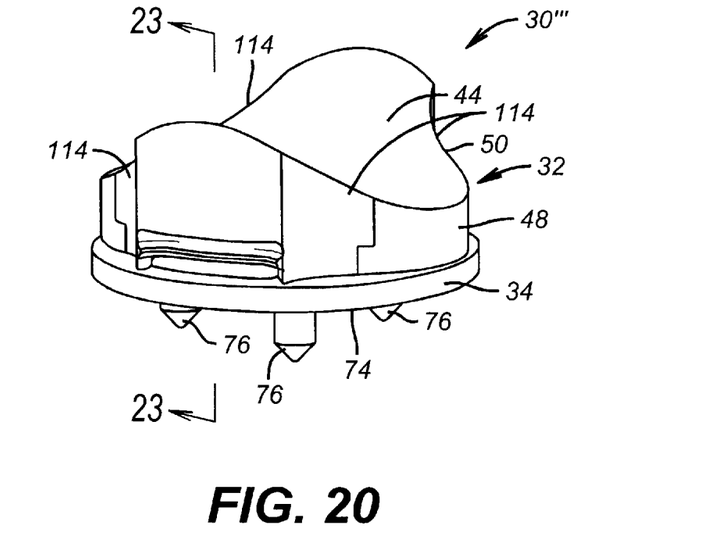
FIG. 20 is an isometric view of an alternate embodiment of the prosthesis illustrated in FIG. 1.
Figure 21:
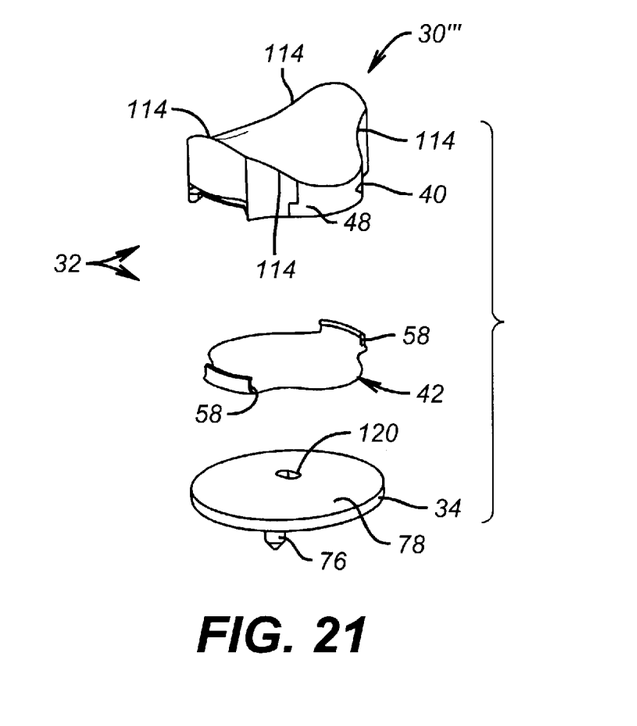
FIG. 21 is an exploded view of the prosthesis illustrated in FIG. 20.
Figure 22:
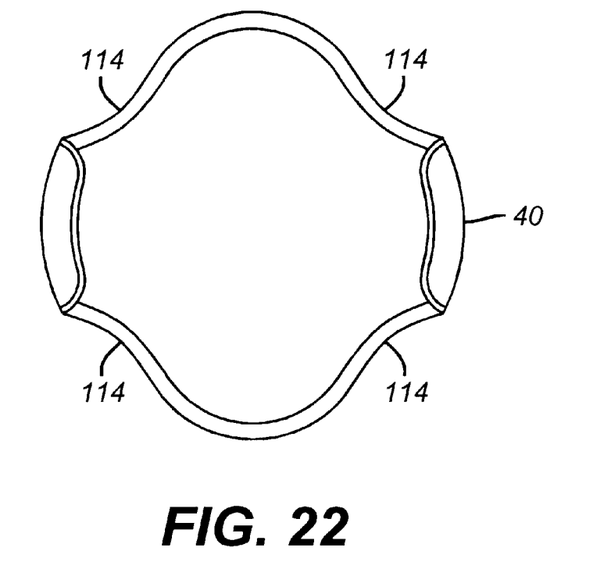
FIG. 22 is bottom view of the patellar bearing member of the prosthesis illustrated in FIG. 20.

It should be noted that a variety of other design considerations are considered within the scope of the present invention. For example, in the embodiment illustrated in FIGS. 20 through 23, a different style of implantable patellar prosthesis 30 is illustrated and labeled 30'". In this embodiment, a three component design is utilized in which a patella insert 42 is used between a patella bearing portion 40 and base component 34. However, the patella bearing portion 40 and patella insert 42 have a unique profile as viewed from the top or bottom. Instead of having a generally circular profile, perimeter surface 48 undulates to form four regions 114 that are radially recessed from what would otherwise be a circular profile. (See FIGS. 20 and 22). Each recessed region 114 is formed generally between each superior-inferior region and the next adjacent medial-lateral region of the saddle configuration of articulation surface 44. Patella insert 42 is designed with a generally matching configuration when viewed from the top or bottom.

Figure 23:
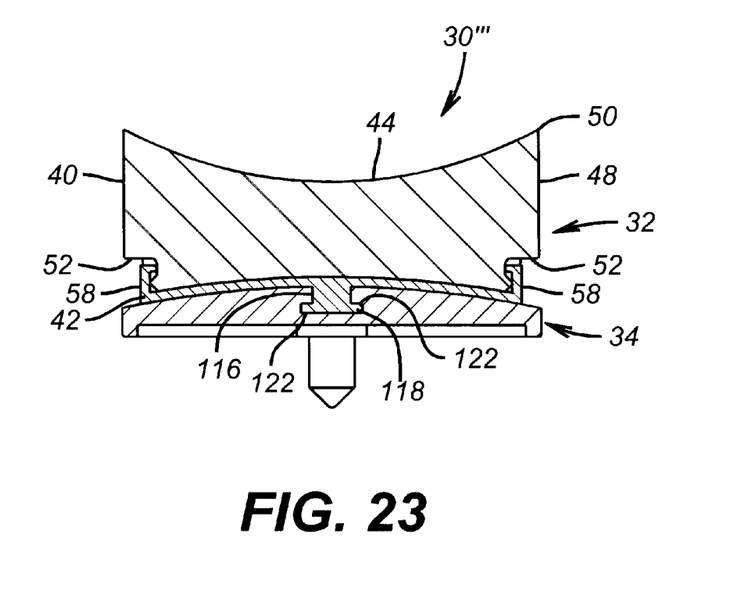
FIG. 23 is a cross-sectional view taken generally along line 23—23 of FIG. 20.

In this embodiment, patella insert 42 is designed with a retention pin 116 having an expanded head portion 118, e.g., a T-pin configuration, as best illustrated in FIG. 23 and as described above. In this embodiment, base component 34 includes an opening 120 (see FIG. 21) that does not extend the entire axial distance through base component 34. Rather, opening 120 is sized and configured to receive head portion 118 therethrough and includes internal grooves 122 that permit the T-shaped head portion 118 to be pivoted into an engaged relationship with base component 34. Optionally, opening 120 can be extended in the form of a slot that would permit movement in the medial-lateral direction as well as angular movement of articulation component 32 relative to base component 34. Again, the interface between base component 34, patella insert 42 and patella bearing portion 40 can be changed to accommodate various materials and other design considerations.

It will be understood that the foregoing description is of exemplary embodiments of this invention, and that the invention is not limited to the specific forms shown. For example, a variety of features in the various embodiments may be combined with features of other embodiments depending on design considerations; the materials utilized for each of the prosthesis components may vary according to design parameters and the advent of new materials; the configuration of the various coupling mechanisms may be adjusted to facilitate the desired relative motion between the articulation component and the base component for providing more comfortable operation of the prosthetic device and/or reduction of stresses acting on the prosthetic device; and two component, three component or multiple component designs may be designed within the scope of the present invention. These and other modifications may be made in the design and arrangement of the elements without departing from the scope of the invention as expressed in the appended claims.

What is claimed is:

1. An implantable patellar prosthesis, comprising:
   a base component having a bone engaging surface adapted for fixation to patellar bone and a joint motion surface oppositely disposed from the bone engaging surface;
   an articulation component removeably connectable to the base component and comprising a bearing component connected to a patella insert;
   the patella insert having a joint motion surface adapted to slideably articulate with the joint motion surface of the base component; and
   the bearing component having an articulation surface adapted to articulate with a femoral component at a patello-femoral joint.

2. The patellar prosthesis of claim 1 wherein the articulation component slideably articulates in a medial-lateral direction with respect to the base component while the base component is fixed to the patellar bone.

3. The patellar prosthesis of claim 2 wherein the patella insert and bearing component are snapped together.

4. The patellar prosthesis of claim 1 wherein the base component includes a coupling mechanism, and the articulation component includes a coupling mechanism adapted to engage the coupling mechanism of the base component to provide the removeable connection between the base component and articulation component.

5. The patellar prosthesis of claim 4 wherein the coupling mechanisms of the articulation and base components include a retention pin having a T-pin configuration and an elongated slot adapted to receive the retention pin.

6. The patellar prosthesis of claim 5 wherein the articulation component is connected to the base component when the retention pin is inserted into the slot and rotated 90°.

7. The patellar prosthesis of claim 4 wherein the coupling mechanisms of the articulation and base components include: a retention pin having a head with a lengthwise dimension greater than a widthwise dimension; and a slot adapted to receive the head.

8. The patellar prosthesis of claim 7 wherein the slot has a width equal to or greater than the widthwise dimension and less than the lengthwise dimension.

9. An implantable patellar prosthesis, comprising:
a base component having a bone engaging surface adapted for fixation to patellar bone, a joint motion surface oppositely disposed from the bone engaging surface, and a coupling mechanism; and
an articulation component having a coupling mechanism coupled to the coupling mechanism of the base component, a joint motion surface adapted to slideably articulate with the joint motion surface of the base component, and an articulation surface adapted to articulate with a femoral component at a patello-femoral joint.

10. The patellar prosthesis of claim 9 wherein the articulation surface of the articulation component has a saddle shape adapted to slideably articulate with the femoral component.

11. The patellar prosthesis of claim 9 wherein the coupling mechanism of the articulation and base components form a removeable connection between the base component and articulation component.

12. The patellar prosthesis of claim 9 wherein the joint motion surfaces of the base and articulation components are shaped as partial spheres to permit movement in an arc relative to one another.

13. The patellar prosthesis of claim 12 wherein the coupling mechanisms of the base and articulation components are configured to provide medial-lateral movement between the base component and articulation component while the base component is fixed to the patellar bone.

* * * * *